(12) United States Patent
DeWitt

(10) Patent No.: US 6,183,645 B1
(45) Date of Patent: *Feb. 6, 2001

(54) METHODS AND APPARATUS FOR LIQUID PHASE SEPARATION

(76) Inventor: Sheila H. DeWitt, 51 Sandbrook Headquarters Rd., Stockton, NJ (US) 08559

( * ) Notice: Under 35 U.S.C. 154(b), the term of this patent shall be extended for 0 days.

This patent is subject to a terminal disclaimer.

(21) Appl. No.: 09/196,094

(22) Filed: Nov. 19, 1998

Related U.S. Application Data

(63) Continuation-in-part of application No. 08/666,194, filed on Jun. 19, 1996, now Pat. No. 5,874,004.

(51) Int. Cl.$^7$ ...................................... B01D 11/00
(52) U.S. Cl. ................ 210/634; 210/644; 210/321.6; 210/321.84; 422/101; 436/177
(58) Field of Search ................... 210/767, 490, 210/634, 644, 660, 487, 489, 455, 321.6, 321.84; 422/101, 88, 89; 436/177, 178

(56) References Cited

U.S. PATENT DOCUMENTS

| | | |
|---|---|---|
| 3,295,686 | 3/1967 | Krueger . |
| 4,221,670 | 9/1980 | Ziemek . |
| 5,096,585 | 3/1992 | Nguyen . |
| 5,133,934 | 7/1992 | Denton . |
| 5,186,830 | 2/1993 | Rait . |
| 5,240,680 | 8/1993 | Zuckermann . |
| 5,324,483 | 6/1994 | Cody . |
| 5,464,541 | 11/1995 | Aysta . |
| 5,529,694 | 6/1996 | Strickler . |
| 5,874,004 * | 2/1999 | DeWitt ................................ 210/634 |

* cited by examiner

Primary Examiner—Ana Fortuna

(57) ABSTRACT

An apparatus and method for phase separation of two materials is disclosed. The two materials to be separated are positioned in an extraction cartridge and passed through a filter device, the filter device includes a filter disk member positioned adjacent at least one and preferably two frit members. A drying cartridge may be used to dry the separated liquid material after it leaves the extraction cartridge. The invention can be used for reaction workup, quenching, product isolation and purification.

20 Claims, 4 Drawing Sheets

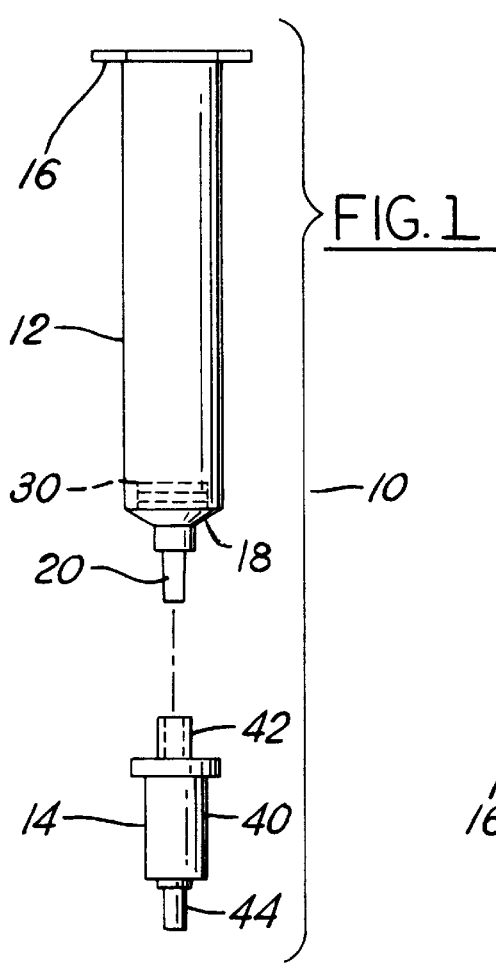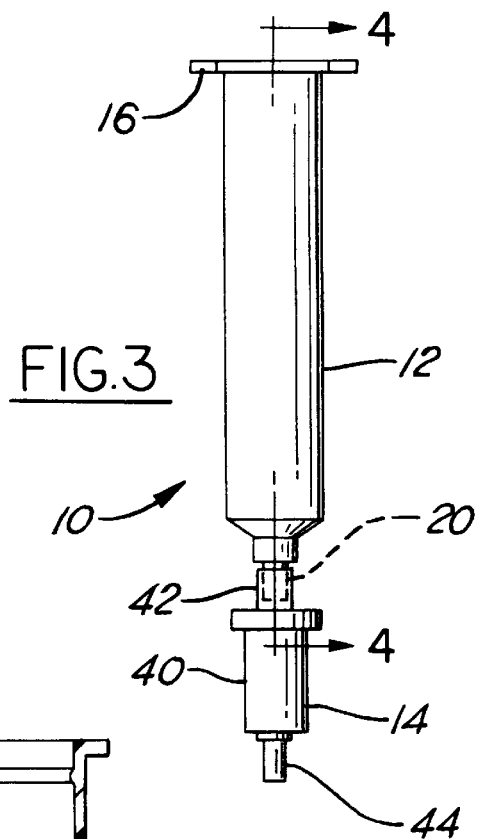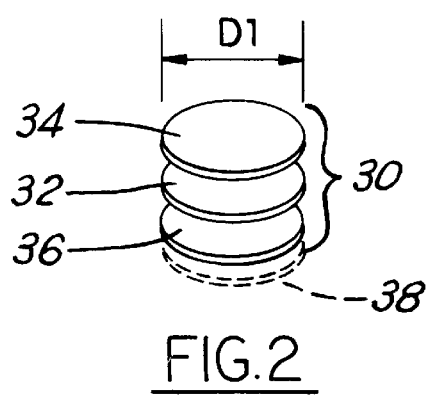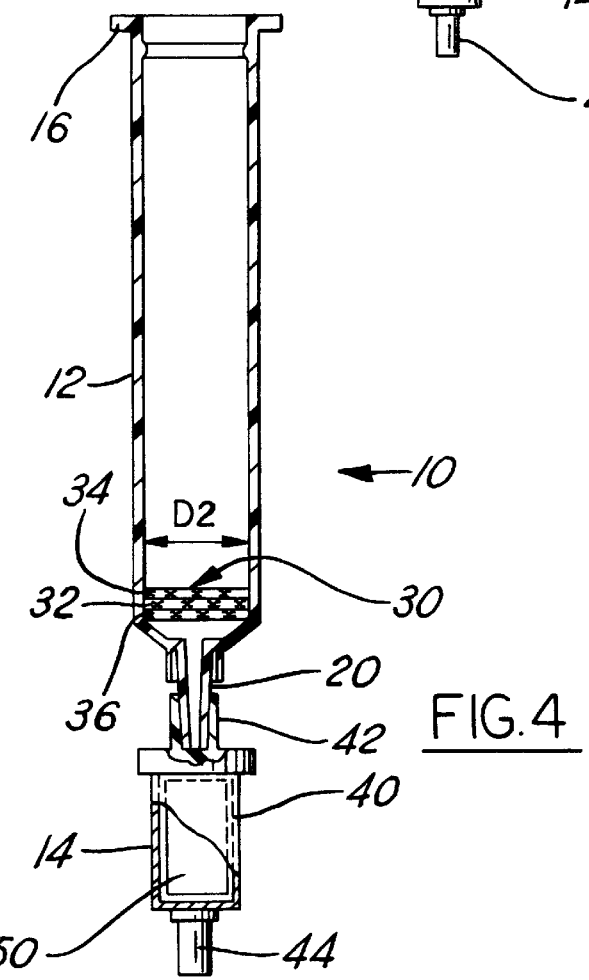
FIG. 1
FIG. 2
FIG. 3
FIG. 4

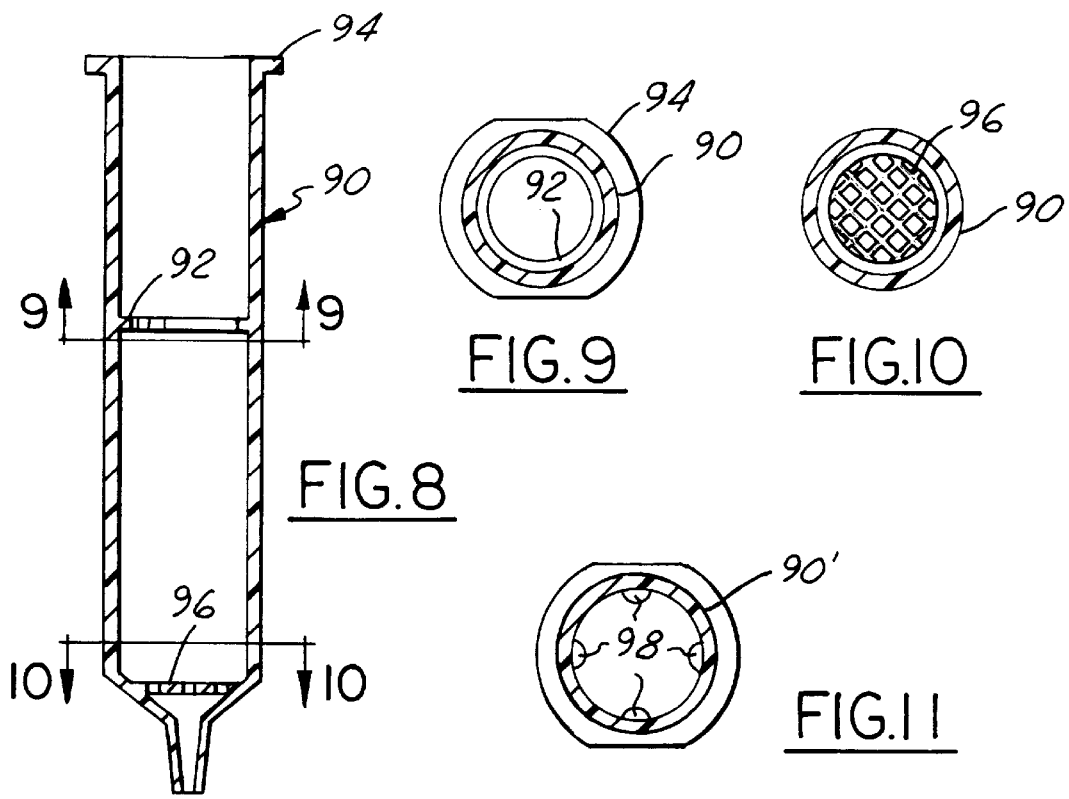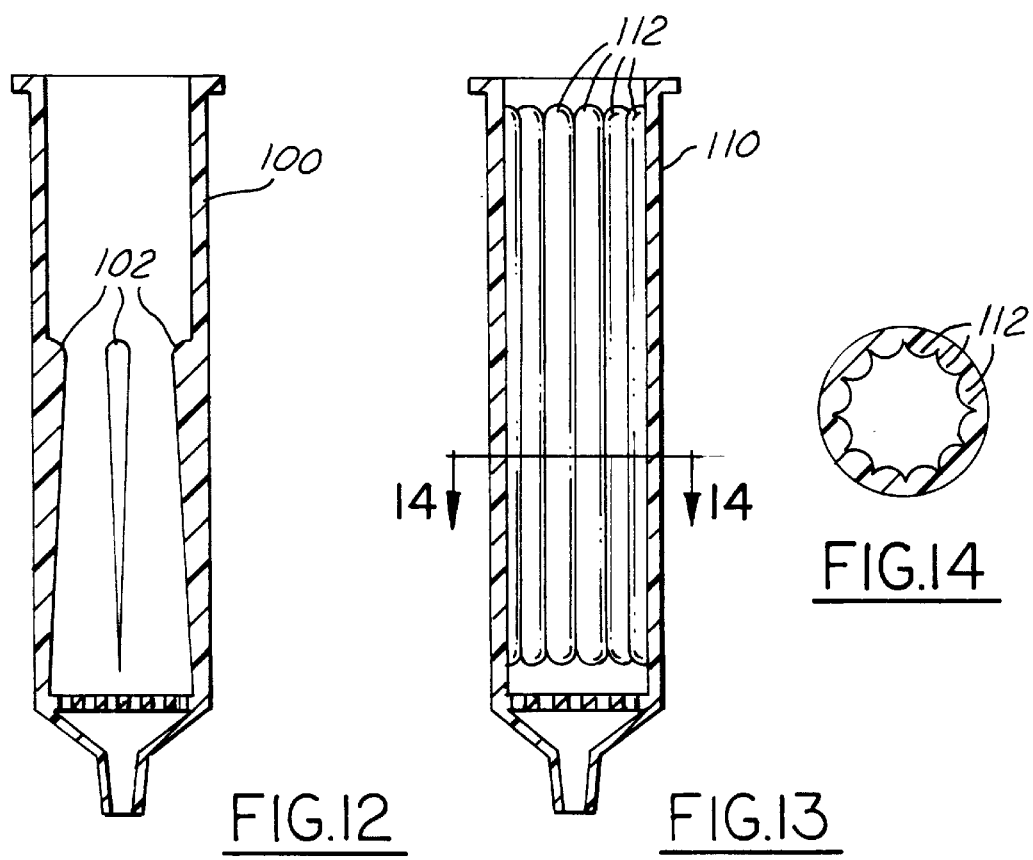

METHODS AND APPARATUS FOR LIQUID PHASE SEPARATION

CROSS-REFERENCE TO RELATED APPLICATION

This application is a continuation in part of U.S. application Ser. No. 08/666,194, filed Jun. 19, 1996, now U.S. Pat. No. 5,874,004, and claims the benefit of International Application No. PCT/US97/10351 filed on Jun. 17, 1997.

TECHNICAL FIELD

The present invention relates to processes and devices for phase separation of materials, particularly for use in multiple, simultaneous synthesis, purification and isolation of compounds.

BACKGROUND ART

Various apparatus and methods are known for the multiple, simultaneous synthesis of compounds, including, but not limited to, organic compounds. Some of the preferred methods and apparatus are shown, for example, in U.S. Pat. No. 5,324,483 entitled "Apparatus for Multiple Simultaneous Synthesis," which is assigned to the same assignee as the present invention. In accordance with that patent, a plurality of compounds are simultaneously synthesized in an array format which is compatible with standard techniques of organic synthesis. The sample handling is carried out using automated systems for speed, accuracy and precision.

The method and apparatus disclosed in the '483 patent can be used for either solid (resin) support or solution based synthesis techniques. The primary steps necessary to perform the synthesis are the development of a synthetic route that will be feasible with the solid or solution techniques utilized, the verification of the synthesis using representative examples, and the execution of the multiple, simultaneous synthesis within an array format to generate the plurality of compounds.

The '483 patent increases the flexibility and diversity of structures that can be produced by parallel, solid phase or solution-based chemical synthesis. Where solution-based chemistry is involved, typically two-phase liquid/liquid extraction protocols are utilized. These techniques are not as easily amenable to automation as techniques using solid or resin-support techniques.

SUMMARY OF THE INVENTION

It is an object of the present invention to provide an improved apparatus and method for phase separation. It is also an object of the present invention to provide a phase separation apparatus and method which is useful for multiple, simultaneous synthesis, purification and isolation.

It is a further object of the present invention to provide a two-phase separation apparatus and method which is more amenable to automation and thus which will facilitate a more efficient and faster simultaneous, multiple synthesis, purification and isolation of compounds.

It is still another object of the present invention to provide a phase separation device which is less expensive and easier to manufacture than known separation devices and which also can be provided a disposable form.

These and other objects are met by the present invention which provides an improved apparatus and method for phase separation of different materials. In accordance with the present invention, a hydrophobic paper filter disk is retained on top of or between porous filter devices in the lower end of a phase extraction cartridge. The cartridge has an open end in which the solution or slurry of materials is introduced, often with a solvent, and a lower end which has an outlet for draining and collection of the separated non-hydrophobic materials. Preferably, the separated material is also passed through a drying cartridge attached to or positioned immediately adjacent the exit of the cartridge.

When used for reaction workup and quenching, the crude reaction mixture is introduced into the cartridge containing an aqueous reaction quenching or workup solution, such as water or saturated ammonium chloride. The introduction of additional solvents or reagents to facilitate a two-phase medium is preferred when using aqueous miscible reaction solvents or mixtures. The heavier materials are separated by passing through the frits and hydrophobic paper filter disk, and the separated material is then dried by passing it through the drying cartridge.

These and other features and benefits of the present invention will become apparent when the following description is viewed in accordance with the attached drawings and appended claims.

BRIEF DESCRIPTION OF THE DRAWINGS

FIG. 1 is an exploded view showing the phase separation cartridge and drying cartridge;

FIG. 2 is an exploded view of the unique filter device;

FIG. 3 is a plane view showing the extraction container and drying cartridge assembled together;

FIG. 4 is a cross-sectional view of the invention shown in FIG. 3, the cross-sectional view being taken along lines 4—4 of FIG. 3 and in the direction of the arrows.

FIG. 8 illustrates still another embodiment of the invention;

FIGS. 9 and 10 are cross-sectional views of the device shown in FIG. 8 with the cross-sections taken along lines 9—9 and 10—10, respectively, in FIG. 8 and in the direction of the arrows;

FIG. 11 illustrates an alternate interior configuration for the cartridge;

FIGS. 12 and 13 illustrate still further alternate interior configurations for the cartridge;

FIG. 14 is a cross-sectional view of the device shown in FIG. 13 with the cross-section being taken along line 14—14 in FIG. 13 and in the direction of the arrows.

BEST MODE(s) FOR CARRYING OUT THE INVENTION

Figure 6:
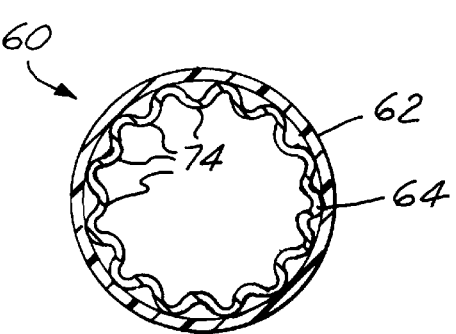
FIG. 6 is a cross-section of the device shown in FIG. 5 with the cross-section taken along line 6—6 in FIG. 5 and in the direction of the arrows.

The apparatus or device used with the present invention is shown in FIGS. 1–4 and indicated generally by the reference number 10. The device 10 includes an extraction cartridge 12 and a drying cartridge 14. The extraction cartridge 12 is an elongated thin walled container, preferably made from glass or a plastic material. If the extraction cartridge 12 is going to be reused, then preferably it is made from glass or a plastic material such as polypropylene which can be adequately cleaned, sterilized and reused. If the extraction cartridge 12 is disposable, then preferably, it is made from a plastic material such as polyethylene or polypropylene.

The extraction cartridge may have a ledge or lip 16 at its open end to facilitate manual handling and/or automation. The cartridge 12 has a funnel or cone-shaped structure 18 at the opposite end which terminates in a material discharge orifice or outlet 20. The outlet 20 can have any desired shape, but preferably has a tapered shape as shown in FIG. 1 in order to mate with a drying cartridge 14 (as explained below).

The phase separation mechanism is shown in more detail in FIG. 2 and designated by the reference numeral 30. The phase separation mechanism or apparatus includes a thin circular wafer-like hydrophobic paper disk 32 placed on top of or sandwiched between a pair of thin wafer-like frit members 34 and 36. Preferably, the frit members 34 and 36 are polypropylene frits, but the frit members can be made of any other conventional filtering material, such as Teflon or glass.

The paper filter disk member 32 can be made from any conventional material, but preferably is a silicone treated product, such as the phase separator product from Whatman International, Ltd., Maidstone, England.

Alternatively, another layer, such as a mesh or screen member could be used for reinforcement, if desired. Such a fourth disk member is shown in dotted lines in FIG. 2 and indicated by the reference numeral 38. If desired, as an embodiment, one or more thin wafer-like mesh or screen members could be used in place of the frits 34 and 36.

In use, preferably three layers 32, 34, and 36 are provided and positioned closely together to form a sandwich or laminated type structure. The diameter D1 of the filter device 30 is the same as the inside diameter D2 of the extraction cartridge 12. In this regard, it is preferable that the filter device 30 be sized to contact the inside walls of the extraction cartridge in order to prevent leakage of materials around the device and through the outlet 20.

If only two members are utilized, i.e. one filter disk member 32 and one frit member, then it is preferred that the frit member be positioned below the filter disk member (i.e. on the downstream sides of the filter disk member). Also, it is possible to utilize two or more laminated phase separation mechanisms 30 in the extraction cartridge 12 to insure better separation, although this might slow down the speed of the separation process.

The drying cartridge 14 is also preferably made from a plastic or glass material. The drying cartridge 14 includes a hollow cylindrical body 40, an inlet 42 and an outlet 44. Cartridges of this type are commercially available. Alternatively, a conventional chemical drying material, such as sodium sulfate ($NaSO_4$), which removes residual water from hydrophobic solvents and reagents, may be placed in the body 40. Some conventional drying cartridges use a paper drying member, such as member 50 shown in FIG. 4.

The inlet 42 of the drying cartridge is adapted to mate with the outlet 20 of the extraction cartridge 12. The outlet 44 of the drying cartridge 14 allows the separated material to flow into a collector vessel of some type, such as a beaker or test-tube (not shown) after the separated material is dried by the drying member 50.

If desired, the final separated product could be further purified by conventional means, such as chromatography.

The present invention is an alternative to two-phase liquid/liquid quench and extraction protocols. Solutions of this type from which liquid/liquid extraction protocols include, for example, oil or oil-based materials and water.

The present invention can also be utilized for heavier than water extractions, such as dichloromethane (or $CH_2Cl_2$) (a/k/a methylene chloride and DCM). DCM is a solvent commonly used in organic synthesis reactions.

An alternative use of the present invention is for the extraction of byproducts from aqueous soluble salts by repeated introduction (and draining) of hydrophobic solvents to the aqueous materials retained in the cartridge. The salts can later be liberated by neutralization and extracted with hydrophibic solvents as described earlier.

The present invention is amenable to automation. This is due to its structure, simplicity, and ease of operation. It is particularly useful for compound workup and separation techniques. For example, for an automated reaction workup, a material, such as a reaction mixture in solution with THF (tetrahydrofuran), can be quenched with, for example, saturated ammonium chloride (sat. $NH_4Cl$), diluted with DCM and extracted. The DCM layer containing the desired product is allowed to separate through the filter device 30 in the extraction cartridge 12. The drying cartridge 14 extracts any water which may be in solution with the dichloromethane thus allowing separation of the dry amine in the DCM.

Initially, the reaction mixture is placed in solution with, for example, tetrohydrofuran (THF) and the mixture is then introduced into the extraction cartridge 12 already containing the saturated ammonium chloride or other quenching material.

An example was carried out utilizing a prototype of the present invention in order to show its usefulness and attributes. The example also demonstrates the ability and invention to be used for parallel processing. In this regard, the phase separation device was used to synthesize and purify imines generated from Grignard reactions.

In this example, a material of 5-nitroanthranilonitrile was dissolved in 1.0 mls of tetrahydrofuran (THF). The two materials were placed in a 10 ml vial. A stir bar and argon blanket were applied. Then, 0.4 ml of 3.0 molar of phenylmagnesium bromide in THC was added to the mixture in the vial. The color change was noted from red to brown to black. An additional 1 ml of THF was added to facilitate stirring.

The reaction was monitored by thin layer chromatography (TLC). After 30 minutes, one-half of the reaction mixture was transferred to a reaction cartridge 12 assembled with a drying cartridge 14 in accordance with the present invention. The reaction was quenched when added to an aqueous solution of saturated ammonium chloride ($NH_4Cl$) already residing in the phase extraction cartridge. DCM was introduced to this mixture to extract the desired product. The phase separation mechanism 30 included two polypropylene frit members 34 and 36, and one silicon treated paper filter disk member 32.

The imine dissolved in DCM and was separated from the material in the extraction cartridge and passed into and through the drying cartridge through outlet 20. The material was collected in a conventional container.

Figure 5:
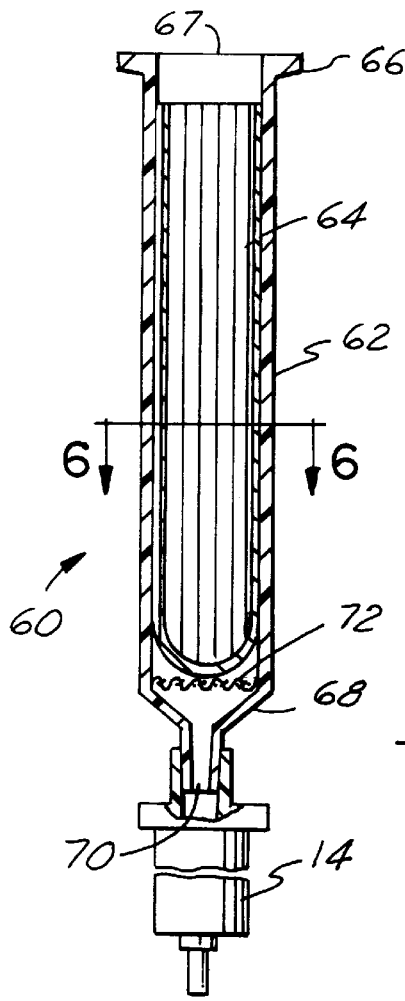
FIG. 5 illustrates an alternate embodiment of the invention useful for lighter-than-water applications.

Cartridge and filter devices for use with lighter-than-water applications as well as heavier-than-water applications are shown in FIGS. 5–15. One preferred embodiment is depicted in FIGS. 5 and 6 and indicated by the reference number 60.

The device 60 has a separation cartridge 62 which is similar in size, shape and material to cartridge 12 described above with reference to FIGS. 1–4. The cartridge 62 has a ledge 66 at its open end and a funnel or cone-shaped structure 68 at the opposite end terminating in a discharge orifice 70.

The phase separation mechanism comprises a cup or thimble-shaped filter device 64 which is positioned inside the cartridge 62. The thin-walled thimble 64 is made of a hydrophobic paper material, and preferably is made of the same material described above with reference to filter disk member 32.

A perforated support member 72 is positioned near the bottom of the cartridge 62 in order to support the thimble filter device 64 therein and also prevent the device 64 from wedging or sealing against the interior walls of the cartridge. The support member 72 can be any perforated member, such as a mesh or screen member, or another filter member which would allow the separated materials to pass through it, such as a polypropylene frit.

In the embodiment shown in FIGS. 5 and 6, the thimble filter member 64 has a plurality of flutes or ridges 74 around its outside circumference. The flutes 74 allow the outside of the thimble to be spaced in most places from the inside wall of the cartridge and thus allow the separated materials to flow more easier and quickly down the cartridge toward the outlet 70. The flutes avoid surface tension and/or capillary action being created between the walls of the cartridge and the outer surface of the thimble.

The flutes on the thimble also provide a greater surface area for materials to pass through the walls. The flutes further aid in accurately centering the thimble in the cartridge which his necessary for manual or automatic dispensing of liquids into the device 60. This will assure reproducible and accurate liquid transfer into the thimble.

Preferably, the cartridge should have a capacity or volume of 12 milliliters, or approximately 1.0 ml, for a 96-well plate format. The porosity of the frit/support member 72 should be about 100 micron. The porosity of the filter paper for the thimble should be known and the inside dimensions of the thimble should accommodate approximately 10 ml of liquid. The length (height) of the thimble should be approximately the same as, or just below the height of, the cartridge (or 96-well plate).

In use, a drying device may also be used with the device 60. The preferred drying device is described above with reference to FIGS. 1–4 and identified by the reference number 14.

Alternate shape and types of thimble filter members are shown in FIGS. 7A, 7B, 7C and 7D. All of these are adapted to fit with a container device, such as cartridge 62. Thimble member 80 (FIG. 7A) is a plain, smooth-walled, cup-shaped device, while thimble member 82 (FIG. 7B) has four wedge-shaped or angled ridges 83 positioned around its outside surface. The ridges 83 are similar to the flutes 74 described above and fulfill the same purposes.

Figures 7A, 7B, 7C, 7D:
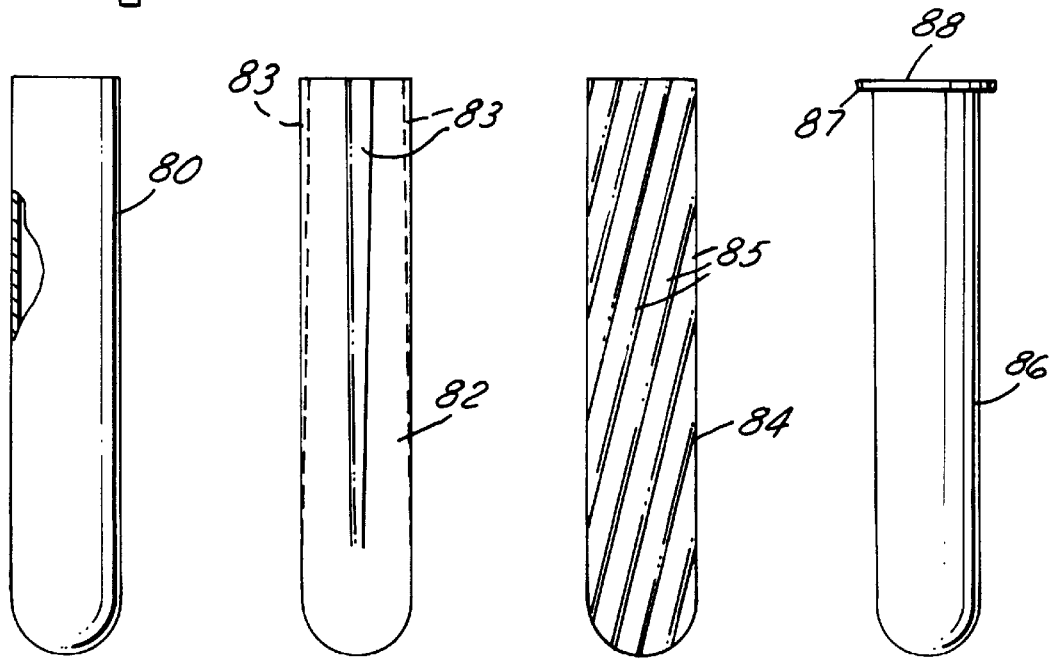
FIGS. 7A, 7B, 7C and 7D illustrate alternate embodiments of thimble or cup-shaped filter devices.

In FIG. 7C, the thimble member 84 has a plurality of angled or spiral-shaped flutes or ridges 85 around the outer surface. The spiral flutes 85 are for the same purposes as the flutes 74 and ridges 83 described above. Finally, FIG. 7D illustrates that the thimble member 86 can have a lip or ridge 87 on its upper end 88. The lip 87 can be adapted to fit over the upper end 67 of cartridge 62, or can be adapted to fit inside the cartridge 62 and thus assist in centering the filter device in the cartridge and at the same time space the outer walls of the filter device from the inner walls of the cartridge.

FIG. 8, in combination with the cross-sectional views shown in FIGS. 9 and 10, depicts another alternate embodiment of a cartridge 90 which can be used with the present invention. The cartridge 90 can be used with any of the thimble filter members described above (as can any of the cartridge members 100 and 110 described below).

Cartridge member 90 has an annular ring member 92 integrally built or molded into its inner chamber which is used to center the thimble filter device positioned in it and also to space the filter device from the inner walls of the cartridge.

The cartridge 90 also has a handling ledge or lip 94 at its upper end and an integrally molded or built-in perforated support member 96 at its lower end.

Rather than supply an entire annular ring around the inner surface of the cartridge, a series or plurality of nubs or projections 98 could be provided instead. This is shown in FIG. 11 with reference to cartridge 90'.

FIGS. 12–14 illustrate still further embodiments of cartridge devices which have means for centering and spacing thimble filter devices therein. Cartridge 100, as shown in FIG. 12, has a series or plurality of uniformly spaced angled ridges 102. Cartridge 110, as shown in FIGS. 13 and 14, has a plurality of elongated ribs or ridges 112 positioned along the inside surface.

Figure 15A:
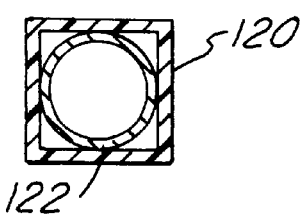
FIGS. 15A, 15B and 15C illustrate representative additional cross-sectional sizes and shapes for the separation cartridge and thimble filter cup in accordance with the present invention.
Figure 15B:
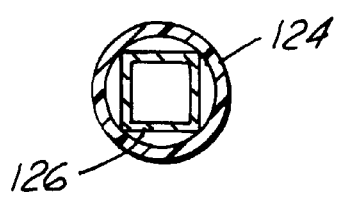
Figure 15C:
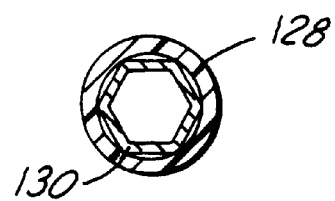

Although all of the embodiments of the invention described above utilized separation cartridges of circular cross-sections and thimble filter cups of generally circular cross-sections, it is to be understood that cartridges and filter cups of other cross-sectional sizes and shapes could be utilized and still achieve the purposes and benefits of the present invention. In this regard, representative additional sizes and cross-sectional shapes of the two components are shown in FIGS. 15A, 15B and 15C. In FIG. 15A, the separation cartridge 120 has a square cross-section, while the filter cup 122 has round or circular cross-section. In FIG. 15B, the separation cartridge 124 has a round cross-section, while the filter cup 126 has a square cross-section. And in FIG. 15C, the separation cartridge 128 has a six-sided hexagonal cross-section. In each of these embodiments, the respective shapes of the components retain the filter cups in centered positions in the cartridges and also space the majority of the outer surfaces of the filter cups from the inner walls of the cartridges.

When the phase separation devices shown in FIGS. 5–15 are utilized, the material dissolved in an aqueous solution is introduced (manually or by an automatic system, such as a liquid handling robot) into the hollow interior cavity or chamber of the thimble filter device in the cartridge. If the material is extracted with a lower density solvent, then the material will separate into a layer above the layer of water in the cartridge. The filter paper forming the thimble allows only the lighter-than-water organic solvents to penetrate and flow through the lower end of the cartridge into the drying device 14. The material flows through the upper walls of the filter device (i.e. the upper portions of the walls above the level of water) and exits through the outlet 70.

Since the thimble filter devices are hydrophobic, the devices shown in FIGS. 5–15 can be used for phase separation of any materials between an aqueous and organic solution, whether the solvents are lighter or heavier-than-water. In this regard, the devices depicted in FIGS. 5–15 can be utilized for the same solutions as the devices depicted in FIGS. 1–4, and can secure all of the same benefits and advantages.

With the present invention, the phase separation device can also be used to wash aqueous soluble components out of a higher or lower density organic solvent to enable purification of organic materials.

While the best modes for carrying out the invention have been described in detail, those familiar with the art to which this invention relates will recognize various alternative designs and embodiments for practicing the invention as defined by the following claims.

What is claimed is:

1. A method for reaction quench and liquid/liquid separation comprising the steps of:
   (a) providing an extraction cartridge, said extraction cartridge comprising an elongated container with a filter member and at least one porous support member positioned inside, said filter member being cup-shaped and made from a hydrophobic non-absorbing material, and said support member supporting said filter member in said container;
   (b) introducing a reaction mixture into the extraction cartridge container, said reaction mixture having a first liquid material and a second liquid material;
   (c) quenching said reaction mixture; and
   (d) separating said first liquid material from said second liquid material by passing said first liquid material through said filter member in said extraction cartridge.

2. The method as set forth in claim 1 wherein said first liquid material is non-aqueous and said second liquid material is aqueous.

3. The method as set forth in claim 2 wherein said reintroduction of said first liquid into said container and repeating steps (c) and (d) is repeated at least two times.

4. The method as set forth in claim 3 wherein said reintroduction of said first liquid into said container and repeating steps (c) and (d) is repeated at least two times.

5. The method as set forth in claim 1 further comprising the step of purifying said first liquid material.

6. The method as set forth in claim 1 wherein separation of said first and second liquid materials is accomplished by gravity.

7. The method as set forth in claim 1 further comprising the step of introducing said first liquid material back into said extraction cartridge container and thereafter repeating steps (c) and (d).

8. The method as set forth in claim 7 wherein said reintroduction of said first liquid into said container and repeating steps (c) and (d) is repeated at least two times.

9. The method as set forth in claim 1 further comprising the step of introducing a third liquid material into said second liquid material following said separation of said first liquid material and forming a second reaction mixture, and thereafter quenching said second reaction mixture and separating said third liquid material from said second liquid material.

10. The method as set forth in claim 9 wherein said first and third liquid materials are non-aqueous and said second liquid material is aqueous.

11. The method as set forth in claim 1 wherein said first liquid material is less dense than said second liquid material.

12. The method as set forth in claim 1 wherein said first liquid material is more dense than said second liquid material.

13. A filter separation device comprising:
   a liquid/liquid separation cartridge member, said cartridge member having an elongated hollow body portion, a necked-down portion, and a smaller discharge portion,
   an elongated hollow cup-shaped hydrophobic filter member positioned inside said separation cartridge, and
   spacing and centering means on the exterior of said filter member for spacing said filter member from said cartridge member and for centering said filter member in said cartridge member.

14. The filter separation device as set forth in claim 13 wherein said spacing and centering means comprises a plurality of flute members positioned on the exterior surface of said filter member.

15. The filter separation device as set forth in claim 13 wherein said spacing and centering means comprises at least one raised annular ring-positioned on the exterior of said filter member.

16. A filter separation device comprising:
   an elongated hollow thin-walled container member having a substantially circular cross-sectional shape; and
   an elongated hollow cup-shaped filter member positioned inside said container member;
   said filter member being made from a hydrophobic non-absorbing material;
   said filter member having a non-circular cross-sectional shape with a plurality of planar side the circumference thereof, wherein said filter member only contacts the inside of said container member at a limited member of locations.

17. The filter separation device as set forth in claim 16 wherein the cross-sectional shape of said filter member is selected from the group comprising a square, pentagon, hexagon, and octagon.

18. A method for two phase liquid/liquid separation comprising the steps of:
   proving a separation cartridge comprising an elongated hollow thin-walled container and a filter member positioned inside said container, said filter member being made from a hydrophobic non-absorbing material and having an elongated hollow cup-shape, and said filter member having spacing and centering means thereon for spacing said filter member from said container and for centering said filter member in said container, said container having an exit port;
   introducing a solution into said filter member in said container, said solution comprising a mixture of a first aqueous liquid and a second liquid which is an organic material immiscible in an aqueous liquid;
   separating said first liquid from said second liquid by passing said second liquid through said filter member and into said container while retaining said first liquid in said cup-shaped filter member, said second liquid passing from said filter member and into the space between said filter member and said container caused by said spacing and centering means; and
   exhausting said second liquid from said container through said exit port.

19. The method as set forth in claim 18 further comprising the steps of collecting said second liquid after it has been exhausted from said exit port; and drying said second liquid.

20. The method as set forth in claim 18 further comprising the step of supporting said filter member in said container with a porous filter member.

* * * * *

UNITED STATES PATENT AND TRADEMARK OFFICE
CERTIFICATE OF CORRECTION

PATENT NO. : 6,183,645 B1
DATED : February 6, 2001
INVENTOR(S) : Sheila H. DeWitt It is certified that error appears in the above-identified patent and that said Letters Patent is hereby corrected as shown below:

<u>Column 8,</u>
Line 24, "planar side the circumference" should be -- planar side members around the circumference --
Line 26, "limited member" should be -- limited number --

Signed and Sealed this

Twenty-sixth Day of February, 2002

Attest:

Attesting Officer

JAMES E. ROGAN
Director of the United States Patent and Trademark Office